United States Patent
Tsuboyama et al.

(10) Patent No.: US 7,279,233 B2
(45) Date of Patent: Oct. 9, 2007

(54) LIGHT-EMITTING MATERIAL AND LIGHT-EMITTING DEVICE

(75) Inventors: Akira Tsuboyama, Kanagawa (JP); Shinjiro Okada, Kanagawa (JP); Takao Takiguchi, Tokyo (JP); Satoshi Igawa, Kanagawa (JP); Jun Kamatani, Tokyo (JP); Manabu Furugori, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 470 days.

(21) Appl. No.: 10/886,570

(22) Filed: Jul. 9, 2004

(65) Prior Publication Data

US 2005/0014024 A1 Jan. 20, 2005

(30) Foreign Application Priority Data

Jul. 15, 2003 (JP) ............................. 2003-196957

(51) Int. Cl.
*H01L 51/54* (2006.01)
(52) U.S. Cl. ...................... 428/690; 428/917; 313/504; 257/E51.041; 257/E51.044
(58) Field of Classification Search ...................... None
See application file for complete search history.

(56) References Cited

FOREIGN PATENT DOCUMENTS

JP 2940514 6/1999

OTHER PUBLICATIONS

Gujadhur et al., "Formation of Aryl-Nitrogen, Aryl-Oxygen, and Aryl-Carbon Bonds Using Well-Defined Copper(I)-Based Catalysts", Organic Letters, 3(26), pp. 4315-4317 and supporting information pp. S1-S13, 2001.*
Ranjan et al., "Synthesis, spectroscopic, photophysical and electrochemical behaviour of ruthenium(II) and copper(I) isocyano-bridged complexes with polypyridine ligands: 2, 2'-bipyridine and 1,10-phenanthroline", Transition Metal Chemistry, 27, pp. 668-675, 2002.*
Chen, et al., "Recent Developments In Molecular Organic Electroluminescent Materials," *Macromol. Symp.* vol. 125, pp. 1-48 (1997).
Jin, et al., "Iodo(1,10-phenanthroline-$N,N^1$)(triphenylphosphine)copper(I)," *Acta. Cryst.* C54, 1087-1089 (1998).
Ma, et al., "High Luminescence Gold(I) and Copper(I) Complexes with a Triplet Excited State for Use In Light-Emitting Diodes," Adv. Mater., vol. 11, No. 10, 852-857 (1999).

* cited by examiner

*Primary Examiner*—Marie Yamnitzky
(74) *Attorney, Agent, or Firm*—Fitzpatrick, Cella, Harper & Scinto

(57) ABSTRACT

There is provided a light-emitting material comprising a metal coordination compound having a partial structure represented by the following general formula (1).

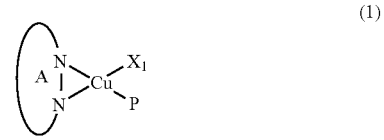

(1)

The light-emitting material has high luminous efficiency and high stability and can be produced at a low cost.

5 Claims, 4 Drawing Sheets

LIGHT-EMITTING MATERIAL AND LIGHT-EMITTING DEVICE

This application claims priority from Japanese Patent Application No. 2003-196957 filed on Jul. 15, 2003, which is hereby incorporated by reference.

BACKGROUND OF THE INVENTION

1. Field of the Invention

The present invention relates to a light-emitting device using an organic compound. More specifically, the present invention relates to a light-emitting device that can provide stability and high efficiency by using a metal coordination compound as a light-emitting material.

2. Related Background Art

Applied studies have been vigorously conducted on organic EL elements as light-emitting devices having high-speed response and high efficiency (see, for example, Macromol. Symp. 125, 1-48 (1997)).

Copper complexes can be manufactured at relatively low costs because their raw materials are available at low costs. Sufficiently exploiting the performance of a copper complex enables a low-cost and high-performance organic EL element to be manufactured.

Organic EL elements using copper complexes are disclosed in Japanese Patent No. 2940514 and Advanced Materials 1999 11 No. 10 p. 852 Y. Ma et al. "High Luminescence Gold (1) and Copper (1) Complexes with Triplet Excited State for Use in Light-Emitting Diodes." However, those EL elements have significantly low luminous efficiency and those publications describe insufficiently the efficiency of those elements. Therefore, it is hard to consider that the properties of the copper complexes are sufficiently exploited. The performance of those elements is not enough for use in displays, lighting, and so on.

Acta Crystallographica Section C C54, 1998, p. 1087 discloses a copper complex having a structure which is relatively similar to that of a compound of the present invention. However, this publication has no description relating to light emission. Moreover, the copper complex cannot be regarded as a light-emitting material because the copper complex emits no light or extremely weak light at room temperature.

SUMMARY OF THE INVENTION

An object of the present invention is to provide a low-cost light-emitting material having high luminous efficiency and high stability.

That is, according to one aspect of the present invention, there is provided a light-emitting material which is a metal coordination compound having a partial structure represented by the following general formula (1):

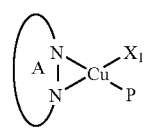

(1)

(wherein:

Cu represents a copper ion;

a ligand A is a bidentate ligand having as its fundamental skeleton 2,2'-bipyridinyl which may have a condensed cyclic group or a substituent;

an atom P that coordinates with Cu is a phosphorus atom of a phosphine compound represented by $PR_1R_2R_3$ ($R_1$, $R_2$, and $R_3$ in $PR_1R_2R_3$ each represent one of a straight-chain, branched, or cyclic alkyl group and an aromatic cyclic group that may have a substituent, and $R_1$, $R_2$, and $R_3$ may be identical to or different from one another. A $CH_2$ group in the alkyl group may be substituted by —O— or —NH—. An H atom may be substituted by an aromatic cyclic group or a halogen atom.);

an atom of $X_1$ that coordinates with Cu is selected from the group consisting of a halogen atom, an oxygen atom, a sulfur atom, and a nitrogen atom; and one of $R_1$, $R_2$, and $R_3$ in $PR_1R_2R_3$ may contain $X_1$ to form a bidentate ligand).

According to another aspect of the present invention, there is provided a light-emitting device having a light-emitting layer containing the above light-emitting material.

DESCRIPTION OF THE PREFERRED EMBODIMENT

Figure 1A:
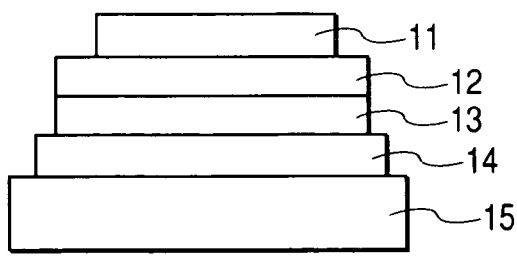
FIGS. 1A, 1B, 1C, and 1D are diagrams each showing an example of a light-emitting device according to an embodiment of the present invention.

Hereinafter, an embodiment of the present invention is described in detail.

First, the characteristics of a metal coordination compound (copper complex) which is a light-emitting material of the present invention are described.

A metal coordination compound of the present invention has a structure in which a nitrogen atom in a ligand A having an aromatic diimine structure and a phosphorus atom in phosphine having a $PR_1R_2R_3$ structure coordinate with monovalent Cu.

A copper ion to be used as a central metal of a copper complex is preferably a +1 valent ion. When the electron configuration of a copper atom is taken into consideration, +1 valent copper should contain 10 d electrons. In general, a transition metal having an even number of d electrons often exhibits good light-emitting property.

The ligand A is preferably selected from the following structural formulae:

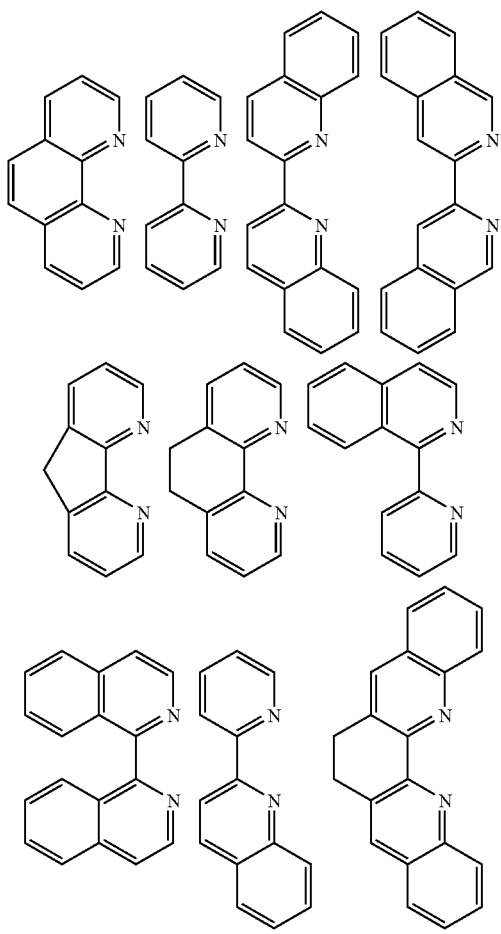

(wherein: each of the above structural formulae has a basic structure and may have a condensed cyclic group or a substituent; the substituent is a halogen atom, a straight-chain, branched, or cyclic alkyl group, or an aromatic cyclic group that may have a substituent; a $CH_2$ group in the alkyl group may be substituted by —O— or —NR— (R represents an alkyl group or an aromatic cyclic group that may be substituted.); and an H atom may be substituted by an aromatic cyclic group or a halogen atom).

The ligand A is more preferably represented by the following structural formula:

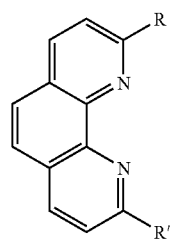

(wherein: R and R' each represent a straight-chain, branched, or cyclic alkyl group or an aromatic cyclic group that may have a substituent, and R and R' may be identical to or different from each other; a $CH_2$ group in the alkyl group may be substituted by —O— or —NH—; an H atom may be substituted by an aromatic cyclic group or a halogen atom; and one of R and R' may be a hydrogen atom).

Specific examples of the ligand A are shown below.

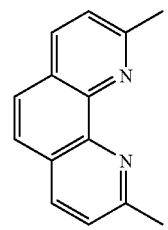

31

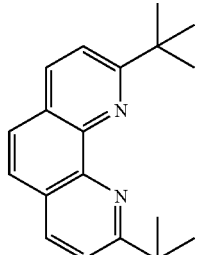

32

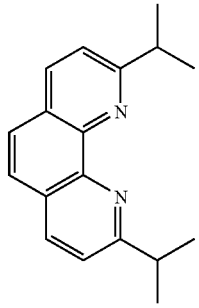

33

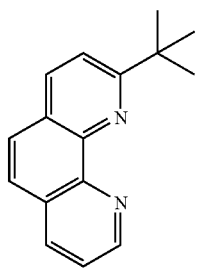

34

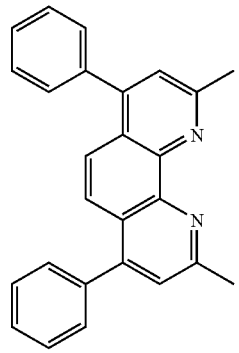

35

36
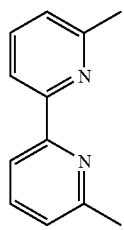
37
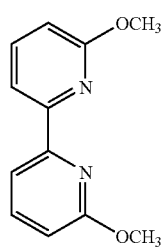
38
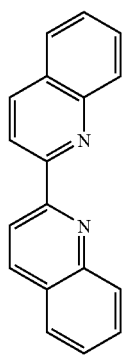
39
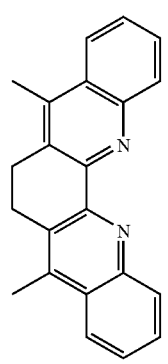
310
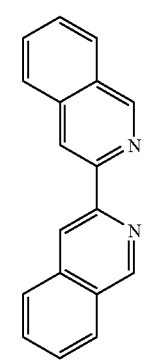
311
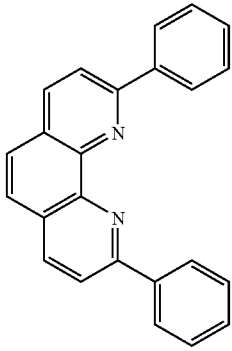
312
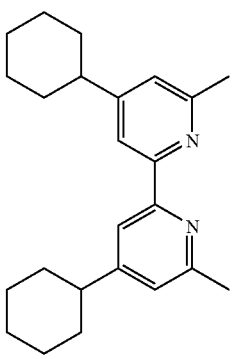
313
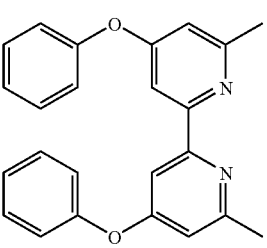
314
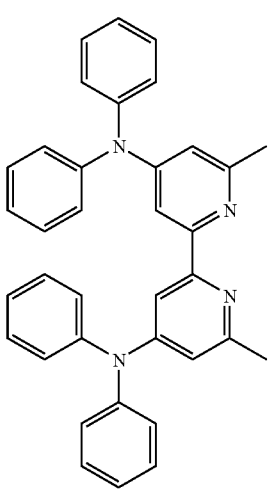

315 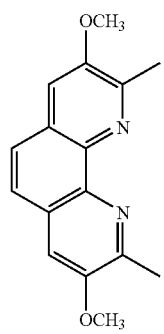
316 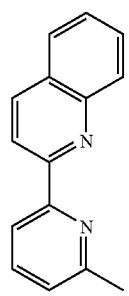
317 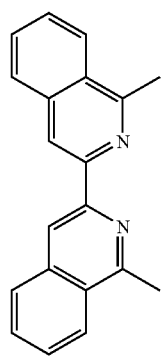
318
319
320 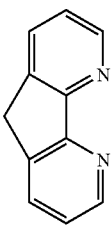
321 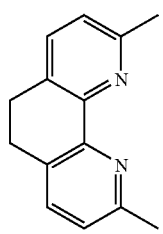
322 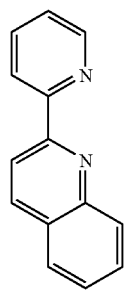
323 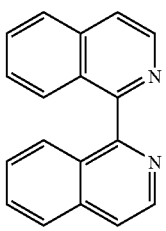
324 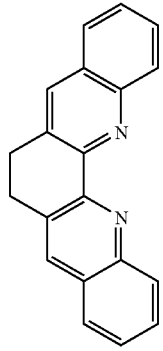

-continued
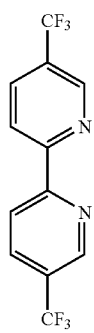
325
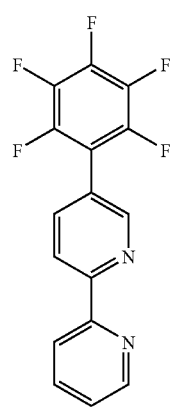
326
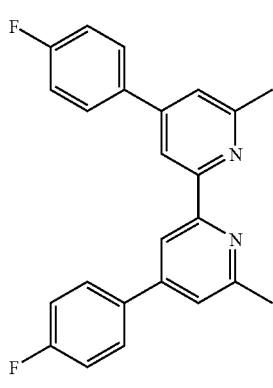
327
Specific examples of a phosphine ligand (monodentate ligand) are shown below.
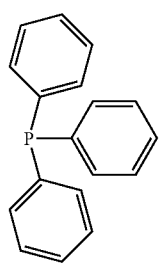
41
-continued
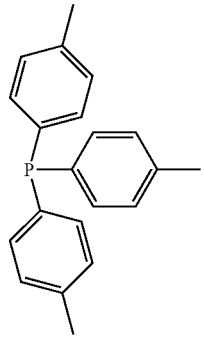
42
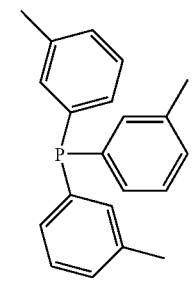
43
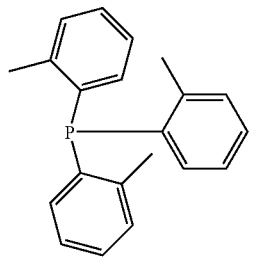
44
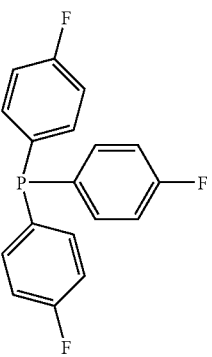
45
46

47
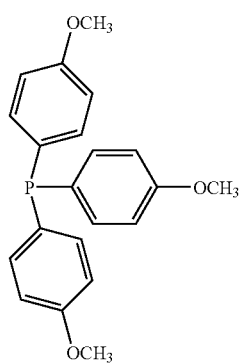
48
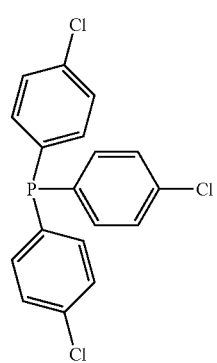
49
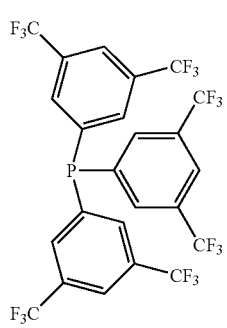
410
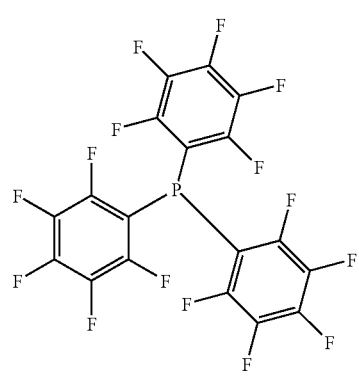
411
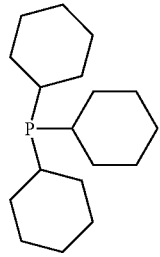
412
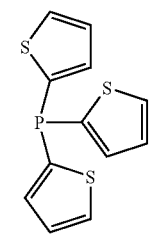
413
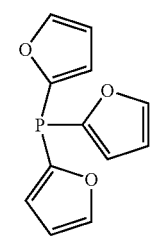
414
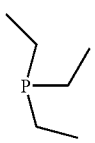
415
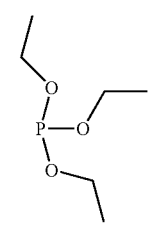
416
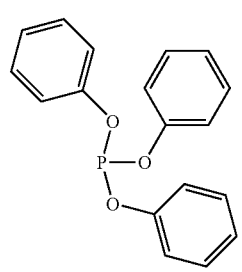

-continued

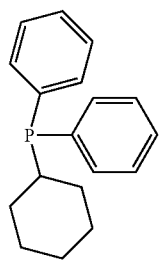
417

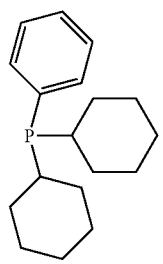
418

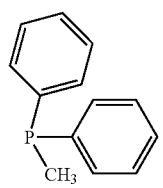
419

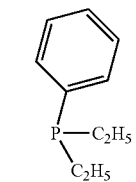
420

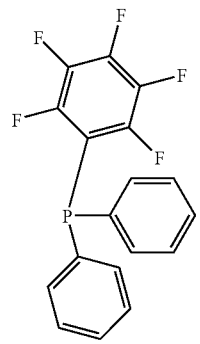
421

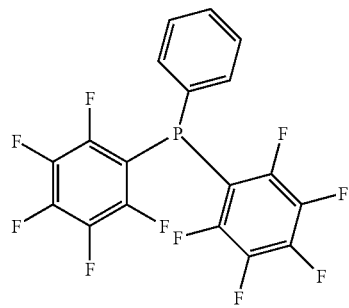
422

-continued

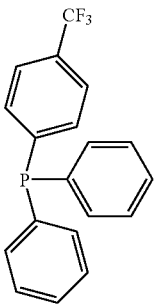
423

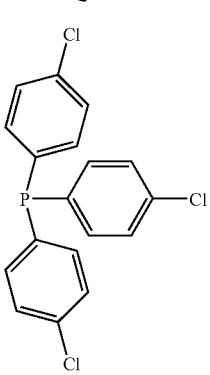
424

The metal coordination compound of the present invention is desirably a neutral and nonionic compound having no counter ion in view of an element preparation process in order to use the compound for a light-emitting device. To achieve this, it is preferable that, because each of the ligand A and the phosphine ligand is a zero valent neutral ligand, $X_1$ be a −1 valent monodentate ligand and the atom of $X_1$ that coordinates with Cu be selected from the group consisting of a halogen atom, a nitrogen atom in an aromatic cyclic group that may have a substituent, an oxygen atom in —OR, and a sulfur atom in —SR(R in —OR or in —SR is a straight-chain, branched, or cyclic alkyl group or an aromatic cyclic group that may have a substituent. A $CH_2$ group in the alkyl group may be substituted by —O— or —NH—. An H atom may be substituted by an aromatic cyclic group or a halogen atom.). Specific examples of $X_1$ are shown below.

—I   51
—Br  52
—Cl  53
—F   54

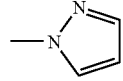
55

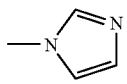
56

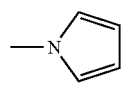
57

-continued
58 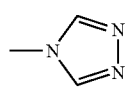
59 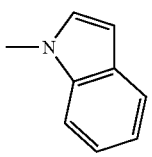
510 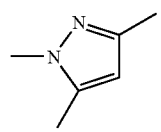
511 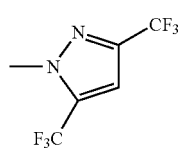
512 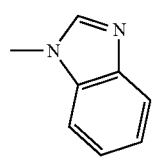
513 —SC₄H₉
514 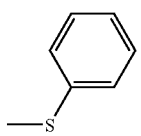
515 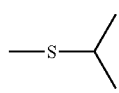
516 —OC₄H₉
517 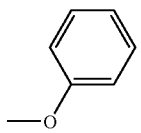
518 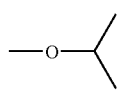
Also, −1 valent bidentate ligands as shown below obtained by adding anionic groups to phosphine are preferable.
61 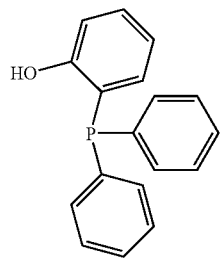
62 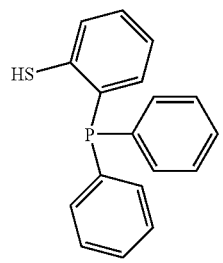
63 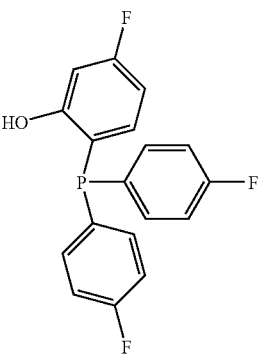
64 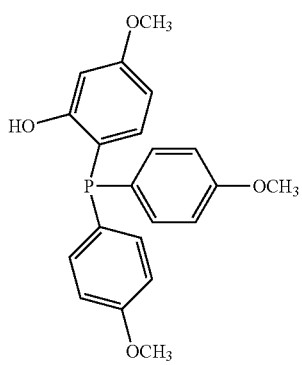

-continued

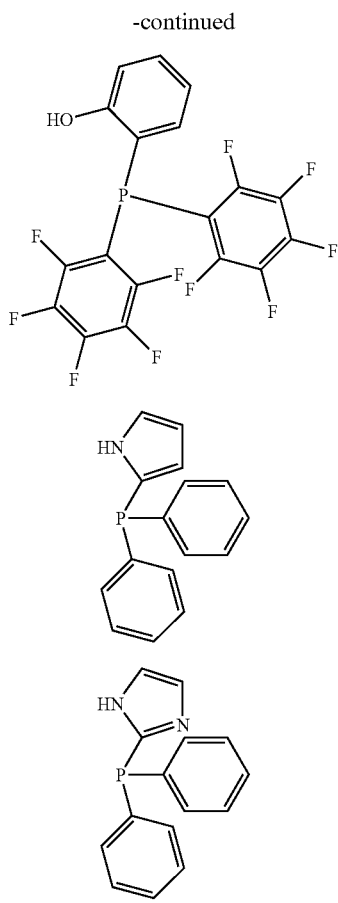

The excited states of the copper coordination compounds having those structures can belong to metal-to-ligand-charge-transfer (MLCT) excited states, so that strong light emission can be obtained. To obtain those excited states, it is desirable that a copper ion easily emit an electron and the electron-acceptability of a ligand that accepts the electron be strong upon excitation. In the case of the copper coordination compound of the present invention, a ligand that accepts an electron is the ligand A having a diimine structure with a long conjugate length and a large electron affinity. For instance, as described above, each of phenanthroline, 2,2'-bipyridine, and derivatives thereof can be used for the ligand. In addition, it is sufficient to allow a ligand having high electron-donating property to coordinate with a Cu ion in order to make it easy for the Cu ion to emit an electron. The phosphine ligand used in the present invention has the property and promotes strong light emission.

To achieve high luminous efficiency, it is important to adopt a ligand structure that suppresses a structural change between a ground state and an excited state. The coordination structure of Cu (1) is a 4-coordination pseudo-tetrahedral structure. High luminous efficiency can be obtained when the structure is maintained in an excited state. For example, in the case where the ligand A is such that 2- and 9-positions of phenanthroline are substituted by two alkyl groups, the ligand has an effect of maintaining a pseudo-tetrahedral structure in a ground state even in an excited state, so that high light-emitting property can be obtained. In an excited state, a tetrahedral structure tends to be a planar structure. However, a structure close to a tetrahedral structure can be maintained by substituting the ligand with a bulky substituent.

In addition, the light-emitting material of the present invention emits extremely strong light in a solid state, in particular, a perfect powder state as compared to a generally used light-emitting material in spite of the fact that the luminous efficiency of the light-emitting material of the present invention in a solution is not high. Probably, this is mainly due to the following two reasons.

One reason is that the coordination structure of Cu (1) in a ground state is a 4-coordination pseudo-tetrahedral structure. When Cu (1) is brought into an excited state by exciting it, Cu (1) forms an MLCT excited state. Therefore, Cu is in a state close to a +2 valent state, so that a structure close to a planar structure is stable. At this time, the structure changes to a large extent between the ground state and the excited state, and the number of heat inactivation paths of energy increases, thereby resulting in weakened light emission. However, the structural change is suppressed because a molecular motion is inhibited in a solid. Therefore, strong light emission may be obtained.

The other reason is that an additional coordination structure is formed in a solution and a 5-coordination structure may be formed. A 5-coordination structure cannot provide strong light emission. Such a 5-coordination reaction is hardly obtained in a solid because a molecular motion is suppressed in the solid. Therefore, strong light emission can be obtained in a solid.

In addition, the Cu coordination compound of the present invention in a powder solid form has an emission lifetime in the range of 0.05 to 50 µsec.

Alumiquinolinol derivatives, coumarin derivatives, quinacridone derivatives, and the like which have been conventionally used can provide extremely strong light emission in solutions, and their strong light-emitting properties are maintained as they are even in solid dispersions. Those properties effectively act even in organic EL elements, so that the high luminous efficiency of the elements can be obtained.

However, in the Cu complex of the present invention, light emission in a solid is extremely strong as compared to that in a solution. The inventors of the present invention have focused on the property and have found that the Cu complex is useful in high-efficiency and stable light emission in an organic EL element.

The Cu coordination compound of the present invention is useful for a light-emitting material for an organic EL element. It is needless to say that the Cu coordination compound has high luminous efficiency. In addition, the Cu coordination compound is suitable for film formation according to an evaporation process and for spin coating for dispersion in a high molecular weight substance. The Cu coordination compound enables stable element preparation because the compound undergoes no damages such as decomposition in an element preparation process. In addition, the inventors have confirmed that the Cu coordination compound poses no problem for the light emission stability of an EL element upon conduction.

As shown in the following examples, the compound of the present invention was found to exhibit excellent performance in terms of stability in a conduction endurance test.

Specific examples of the metal coordination compound of the present invention are shown below.

TABLE 1

| Exemplified Compound No. | Ligand A | Phosphine ligand | $X_1$ |
|---|---|---|---|
| 101 | 31 | 41 | 51 |
| 102 | 31 | 41 | 52 |
| 103 | 31 | 41 | 53 |
| 104 | 31 | 41 | 54 |
| 105 | 31 | 41 | 55 |
| 106 | 31 | 41 | 56 |
| 107 | 31 | 41 | 57 |
| 108 | 31 | 41 | 58 |
| 109 | 31 | 41 | 59 |
| 110 | 31 | 41 | 510 |
| 111 | 31 | 41 | 511 |
| 112 | 31 | 41 | 512 |
| 113 | 31 | 41 | 513 |
| 114 | 31 | 41 | 514 |
| 115 | 31 | 41 | 515 |
| 116 | 31 | 41 | 516 |
| 117 | 31 | 41 | 517 |
| 118 | 31 | 41 | 518 |
| 119 | 31 | 47 | 51 |
| 120 | 31 | 47 | 52 |
| 121 | 31 | 47 | 53 |
| 122 | 31 | 47 | 54 |
| 123 | 31 | 47 | 55 |
| 124 | 31 | 47 | 56 |
| 125 | 31 | 47 | 57 |
| 126 | 31 | 47 | 58 |
| 127 | 31 | 47 | 59 |
| 128 | 31 | 47 | 510 |
| 129 | 31 | 47 | 511 |
| 130 | 31 | 47 | 512 |
| 131 | 31 | 47 | 513 |
| 132 | 31 | 47 | 514 |
| 133 | 31 | 47 | 515 |
| 134 | 31 | 47 | 516 |
| 135 | 31 | 47 | 517 |
| 136 | 31 | 47 | 518 |
| 137 | 33 | 41 | 51 |
| 138 | 33 | 41 | 52 |
| 139 | 33 | 41 | 53 |
| 140 | 33 | 41 | 54 |

TABLE 2

| Exemplified Compound No. | Ligand A | Phosphine ligand | $X_1$ |
|---|---|---|---|
| 141 | 33 | 41 | 55 |
| 142 | 33 | 41 | 56 |
| 143 | 33 | 41 | 57 |
| 144 | 33 | 41 | 58 |
| 145 | 33 | 41 | 59 |
| 146 | 33 | 41 | 510 |
| 147 | 33 | 41 | 511 |
| 148 | 33 | 41 | 512 |
| 149 | 33 | 41 | 513 |
| 150 | 33 | 41 | 514 |
| 151 | 33 | 41 | 515 |
| 152 | 33 | 41 | 516 |
| 153 | 33 | 41 | 517 |
| 154 | 33 | 41 | 518 |
| 155 | 33 | 47 | 51 |
| 156 | 33 | 47 | 52 |
| 157 | 33 | 47 | 53 |
| 158 | 33 | 47 | 54 |
| 159 | 33 | 47 | 55 |
| 160 | 33 | 47 | 56 |
| 161 | 33 | 47 | 57 |
| 162 | 33 | 47 | 58 |
| 163 | 33 | 47 | 59 |
| 164 | 33 | 47 | 510 |
| 165 | 33 | 47 | 511 |
| 166 | 33 | 47 | 512 |
| 167 | 33 | 47 | 513 |
| 168 | 33 | 47 | 514 |
| 169 | 33 | 47 | 515 |
| 170 | 33 | 47 | 516 |
| 171 | 33 | 47 | 517 |
| 172 | 33 | 47 | 518 |
| 173 | 32 | 41 | 51 |
| 174 | 34 | 41 | 51 |
| 175 | 35 | 41 | 51 |
| 176 | 36 | 41 | 51 |
| 177 | 37 | 41 | 51 |
| 178 | 38 | 41 | 51 |
| 179 | 39 | 41 | 51 |
| 180 | 310 | 41 | 51 |

TABLE 3

| Exemplified Compound No. | Ligand A | Phosphine ligand | $X_1$ |
|---|---|---|---|
| 181 | 311 | 41 | 51 |
| 182 | 312 | 41 | 51 |
| 183 | 313 | 41 | 51 |
| 184 | 314 | 41 | 51 |
| 185 | 315 | 41 | 51 |
| 186 | 316 | 41 | 51 |
| 187 | 317 | 41 | 51 |
| 188 | 318 | 41 | 51 |
| 189 | 319 | 41 | 51 |
| 190 | 320 | 41 | 51 |
| 191 | 321 | 41 | 51 |
| 192 | 322 | 41 | 51 |
| 193 | 323 | 41 | 51 |
| 194 | 324 | 41 | 51 |
| 195 | 325 | 41 | 51 |
| 196 | 326 | 41 | 51 |
| 197 | 327 | 41 | 51 |
| 198 | 32 | 41 | 52 |
| 199 | 34 | 41 | 52 |
| 200 | 35 | 41 | 52 |
| 201 | 36 | 41 | 52 |
| 202 | 37 | 41 | 52 |
| 203 | 38 | 41 | 52 |
| 204 | 39 | 41 | 52 |
| 205 | 310 | 41 | 52 |
| 206 | 311 | 41 | 52 |
| 207 | 312 | 41 | 52 |
| 208 | 313 | 41 | 52 |
| 209 | 314 | 41 | 52 |
| 210 | 315 | 41 | 52 |
| 211 | 316 | 41 | 52 |
| 212 | 317 | 41 | 52 |
| 213 | 318 | 41 | 52 |
| 214 | 319 | 41 | 52 |
| 215 | 320 | 41 | 52 |
| 216 | 321 | 41 | 52 |
| 217 | 322 | 41 | 52 |
| 218 | 323 | 41 | 52 |
| 219 | 324 | 41 | 52 |
| 220 | 325 | 41 | 52 |

TABLE 4

| Exemplified Compound No. | Ligand A | Phosphine ligand | $X_1$ |
|---|---|---|---|
| 221 | 326 | 41 | 52 |
| 222 | 327 | 41 | 52 |
| 223 | 32 | 41 | 55 |
| 224 | 34 | 41 | 55 |
| 225 | 35 | 41 | 55 |
| 226 | 36 | 41 | 55 |

TABLE 4-continued

| Exemplified Compound No. | Ligand A | Phosphine ligand | $X_1$ |
|---|---|---|---|
| 227 | 37 | 41 | 55 |
| 228 | 38 | 41 | 55 |
| 229 | 39 | 41 | 55 |
| 230 | 310 | 41 | 55 |
| 231 | 311 | 41 | 55 |
| 232 | 312 | 41 | 55 |
| 233 | 313 | 41 | 55 |
| 234 | 314 | 41 | 55 |
| 235 | 315 | 41 | 55 |
| 236 | 316 | 41 | 55 |
| 237 | 317 | 41 | 55 |
| 238 | 318 | 41 | 55 |
| 239 | 319 | 41 | 55 |
| 240 | 320 | 41 | 55 |
| 241 | 321 | 41 | 55 |
| 242 | 322 | 41 | 55 |
| 243 | 323 | 41 | 55 |
| 244 | 324 | 41 | 55 |
| 245 | 325 | 41 | 55 |
| 246 | 326 | 41 | 55 |
| 247 | 327 | 41 | 55 |
| 248 | 32 | 44 | 51 |
| 249 | 34 | 44 | 51 |
| 250 | 35 | 44 | 51 |
| 251 | 36 | 44 | 51 |
| 252 | 37 | 44 | 51 |
| 253 | 38 | 44 | 51 |
| 254 | 39 | 44 | 51 |
| 255 | 310 | 44 | 51 |
| 256 | 311 | 44 | 51 |
| 257 | 312 | 44 | 51 |
| 258 | 313 | 44 | 51 |
| 259 | 314 | 44 | 51 |
| 260 | 315 | 44 | 51 |

TABLE 5

| Exemplified Compound No. | Ligand A | Phosphine ligand | $X_1$ |
|---|---|---|---|
| 261 | 316 | 44 | 51 |
| 262 | 317 | 44 | 51 |
| 263 | 318 | 44 | 51 |
| 264 | 319 | 44 | 51 |
| 265 | 320 | 44 | 51 |
| 266 | 321 | 44 | 51 |
| 267 | 322 | 44 | 51 |
| 268 | 323 | 44 | 51 |
| 269 | 324 | 44 | 51 |
| 270 | 325 | 44 | 51 |
| 271 | 326 | 44 | 51 |
| 272 | 327 | 44 | 51 |
| 273 | 32 | 44 | 52 |
| 274 | 34 | 44 | 52 |
| 275 | 35 | 44 | 52 |
| 276 | 36 | 44 | 52 |
| 277 | 37 | 44 | 52 |
| 278 | 38 | 44 | 52 |
| 279 | 39 | 44 | 52 |
| 280 | 310 | 44 | 52 |
| 281 | 311 | 44 | 52 |
| 282 | 312 | 44 | 52 |
| 283 | 313 | 44 | 52 |
| 284 | 314 | 44 | 52 |
| 285 | 315 | 44 | 52 |
| 286 | 316 | 44 | 52 |
| 287 | 317 | 44 | 52 |
| 288 | 318 | 44 | 52 |
| 289 | 319 | 44 | 52 |
| 290 | 320 | 44 | 52 |
| 291 | 321 | 44 | 52 |
| 292 | 322 | 44 | 52 |
| 293 | 323 | 44 | 52 |

TABLE 5-continued

| Exemplified Compound No. | Ligand A | Phosphine ligand | $X_1$ |
|---|---|---|---|
| 294 | 324 | 44 | 52 |
| 295 | 325 | 44 | 52 |
| 296 | 326 | 44 | 52 |
| 297 | 327 | 44 | 52 |
| 298 | 32 | 44 | 55 |
| 299 | 34 | 44 | 55 |
| 300 | 35 | 44 | 55 |

TABLE 6

| Exemplified Compound No. | Ligand A | Phosphine ligand | $X_1$ |
|---|---|---|---|
| 301 | 36 | 44 | 55 |
| 302 | 34 | 44 | 55 |
| 303 | 38 | 44 | 55 |
| 304 | 39 | 44 | 55 |
| 305 | 310 | 44 | 55 |
| 306 | 311 | 44 | 55 |
| 307 | 312 | 44 | 55 |
| 308 | 313 | 44 | 55 |
| 309 | 314 | 44 | 55 |
| 310 | 315 | 44 | 55 |
| 311 | 316 | 44 | 55 |
| 312 | 317 | 44 | 55 |
| 313 | 318 | 44 | 55 |
| 314 | 319 | 44 | 55 |
| 315 | 320 | 44 | 55 |
| 316 | 321 | 44 | 55 |
| 317 | 322 | 44 | 55 |
| 318 | 323 | 44 | 55 |
| 319 | 324 | 44 | 55 |
| 320 | 325 | 44 | 55 |
| 321 | 326 | 44 | 55 |
| 322 | 327 | 44 | 55 |
| 323 | 31 | 42 | 51 |
| 324 | 31 | 43 | 51 |
| 325 | 31 | 44 | 51 |
| 326 | 31 | 45 | 51 |
| 327 | 31 | 46 | 51 |
| 328 | 31 | 48 | 51 |
| 329 | 31 | 49 | 51 |
| 330 | 31 | 410 | 51 |
| 331 | 31 | 411 | 51 |
| 332 | 31 | 412 | 51 |
| 333 | 31 | 413 | 51 |
| 334 | 31 | 414 | 51 |
| 335 | 31 | 415 | 51 |
| 336 | 31 | 416 | 51 |
| 337 | 31 | 417 | 51 |
| 338 | 31 | 418 | 51 |
| 339 | 31 | 419 | 51 |
| 340 | 31 | 420 | 51 |

TABLE 7

| Exemplified Compound No. | Ligand A | Phosphine ligand | $X_1$ |
|---|---|---|---|
| 341 | 31 | 421 | 51 |
| 342 | 31 | 422 | 51 |
| 343 | 31 | 423 | 51 |
| 344 | 31 | 424 | 51 |
| 345 | 31 | 42 | 52 |
| 346 | 31 | 43 | 52 |
| 347 | 31 | 44 | 52 |
| 348 | 31 | 45 | 52 |
| 349 | 31 | 46 | 52 |
| 350 | 31 | 48 | 52 |
| 351 | 31 | 49 | 52 |
| 352 | 31 | 410 | 52 |

TABLE 7-continued

| Exemplified Compound No. | Ligand A | Phosphine ligand | $X_1$ |
|---|---|---|---|
| 353 | 31 | 411 | 52 |
| 354 | 31 | 412 | 52 |
| 355 | 31 | 413 | 52 |
| 356 | 31 | 414 | 52 |
| 357 | 31 | 415 | 52 |
| 358 | 31 | 416 | 52 |
| 359 | 31 | 417 | 52 |
| 360 | 31 | 418 | 52 |
| 361 | 31 | 419 | 52 |
| 362 | 31 | 420 | 52 |
| 363 | 31 | 421 | 52 |
| 364 | 31 | 422 | 52 |
| 365 | 31 | 423 | 52 |
| 366 | 31 | 424 | 52 |
| 367 | 33 | 42 | 51 |
| 368 | 33 | 43 | 51 |
| 369 | 33 | 44 | 51 |
| 370 | 33 | 45 | 51 |
| 371 | 33 | 46 | 51 |
| 372 | 33 | 48 | 51 |
| 373 | 33 | 49 | 51 |
| 374 | 33 | 410 | 51 |
| 375 | 33 | 411 | 51 |
| 376 | 33 | 412 | 51 |
| 377 | 33 | 413 | 51 |
| 378 | 33 | 414 | 51 |
| 379 | 33 | 415 | 51 |
| 380 | 33 | 416 | 51 |

TABLE 8

| Exemplified Compound No. | Ligand A | Phosphine ligand | $X_1$ |
|---|---|---|---|
| 381 | 33 | 417 | 51 |
| 382 | 33 | 418 | 51 |
| 383 | 33 | 419 | 51 |
| 384 | 33 | 420 | 51 |
| 385 | 33 | 421 | 51 |
| 386 | 33 | 422 | 51 |
| 387 | 33 | 423 | 51 |
| 388 | 33 | 424 | 51 |
| 389 | 33 | 42 | 52 |
| 390 | 33 | 43 | 52 |
| 391 | 33 | 44 | 52 |
| 392 | 33 | 45 | 52 |
| 393 | 33 | 46 | 52 |
| 394 | 33 | 48 | 52 |
| 395 | 33 | 49 | 52 |
| 396 | 33 | 410 | 52 |
| 397 | 33 | 411 | 52 |
| 398 | 33 | 412 | 52 |
| 399 | 33 | 413 | 52 |
| 400 | 33 | 414 | 52 |
| 401 | 33 | 415 | 52 |
| 402 | 33 | 416 | 52 |
| 403 | 33 | 417 | 52 |
| 404 | 33 | 418 | 52 |
| 405 | 33 | 419 | 52 |
| 406 | 33 | 420 | 52 |
| 407 | 33 | 421 | 52 |
| 408 | 33 | 422 | 52 |
| 409 | 33 | 423 | 52 |
| 410 | 33 | 424 | 52 |

TABLE 9

| Example No. | Ligand A | Phosphine ligand |
|---|---|---|
| 501 | 31 | 61 |
| 502 | 31 | 62 |
| 503 | 31 | 63 |
| 504 | 31 | 64 |
| 505 | 31 | 65 |
| 506 | 31 | 66 |
| 507 | 31 | 67 |
| 508 | 32 | 61 |
| 509 | 32 | 62 |
| 510 | 32 | 63 |
| 511 | 32 | 64 |
| 512 | 32 | 65 |
| 513 | 32 | 66 |
| 514 | 32 | 67 |
| 515 | 33 | 61 |
| 516 | 33 | 62 |
| 517 | 33 | 63 |
| 518 | 33 | 64 |
| 519 | 33 | 65 |
| 520 | 33 | 66 |
| 521 | 33 | 67 |
| 522 | 35 | 61 |
| 523 | 35 | 62 |
| 524 | 35 | 63 |
| 525 | 35 | 64 |
| 526 | 35 | 65 |
| 527 | 35 | 66 |
| 528 | 35 | 67 |
| 529 | 37 | 61 |
| 530 | 37 | 62 |
| 531 | 37 | 63 |
| 532 | 37 | 64 |
| 533 | 37 | 65 |
| 534 | 37 | 66 |
| 535 | 37 | 67 |
| 536 | 38 | 61 |
| 537 | 38 | 62 |
| 538 | 38 | 63 |
| 539 | 38 | 64 |
| 540 | 38 | 65 |
| 541 | 38 | 66 |
| 542 | 38 | 67 |

An example of a method of synthesizing a metal coordination compound of the present invention is shown below. In this example, 2,9-dimethylphenanthroline (31 shown before) is used for the ligand A. 2,9-Dimethylphenanthroline and CuX (X=I, Br, Cl) are allowed to react with each other by using toluene as a reaction solvent to confirm the formation of a red powder. Then, $PR_1R_2R_3$ is added to the reaction mixture. Each of 41 to 424 shown before can be used for $PR_1R_2R_3$. Phosphine ligands except those can also be used. After the addition of $PR_1R_2R_3$, the reaction mixture is refluxed for 3 hours in a stream of nitrogen to precipitate a reactant. The reactant is filtered out and washed with toluene, resulting in a target product.

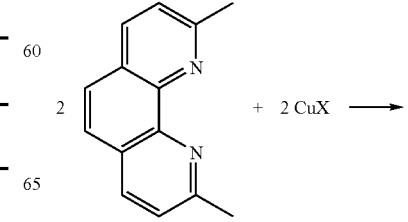

(A)

-continued

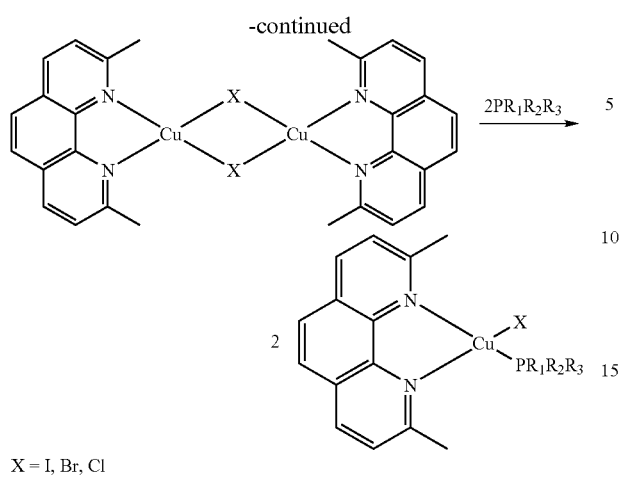

X = I, Br, Cl

Next, a light-emitting device of the present invention is described. The light-emitting device of the present invention is characterized in that a light-emitting layer contains the above light-emitting material, and the light-emitting layer preferably contains 100% of the light-emitting material.

Next, the light-emitting device of the present invention is described with reference to FIGS. 1A to 1D.

In each figure, reference numeral 11 denotes a metal electrode; 12, a light-emitting layer; 13, a hole-transporting layer; 14, a transparent electrode; 15, another transparent electrode; 16, an electron-transporting layer; and 17, an exciton diffusion preventive layer.

FIGS. 1A to 1D each show a basic structure of an organic EL element of the present invention.

As shown in FIGS. 1A to 1D, an organic EL element is generally constructed by laminating the transparent electrode 14 and the metal electrode 11 on the transparent substrate 15 with one or multiple organic layers sandwiched between the transparent electrode 14 and the metal electrode 11.

In FIG. 1A, the organic layers comprise the light-emitting layer 12 and the hole-transporting layer 13. ITO or the like, which has a large work function, is used for the transparent electrode 14 to provide good property of injecting a hole from the transparent electrode 14 into the hole-transporting layer 13. A metallic material with a small work function such as aluminum, magnesium, or an alloy made from them is used for the metal electrode 11 to provide good property of injecting electrons into the organic layers. Those electrodes each have a thickness in the range of 50 to 200 nm.

An alumiquinolinol complex (a representative example thereof is Alq shown below) or the like, which has electron-transporting and light-emitting properties, is used for the light-emitting layer 12. In addition, a material having electron-donating property such as a triphenylamine derivative (a representative example thereof is α-NPD shown below) is used for the hole-transporting layer 13.

The element constructed as described above exhibits rectifying property. When an electric field is applied to the element to set the metal electrode 11 as a cathode and the transparent electrode 14 as an anode, an electron is injected from the metal electrode 11 into the light-emitting layer 12 and a hole is injected from the transparent electrode 14 into the light-emitting layer 12.

The injected hole and electron recombine with each other in the light-emitting layer 12 to generate an exciton, thereby leading to light emission. At this time, the hole-transporting layer 13 serves as an electron-blocking layer. As a result, the recombination efficiency at an interface between the light-emitting layer 12 and the hole-transporting layer 13 increases, resulting in increased luminous efficiency.

Figure 1B:
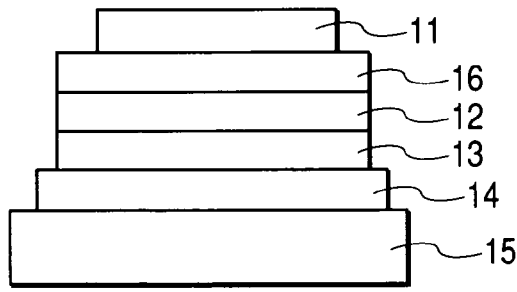

In FIG. 1B, the electron-transporting layer 16 is additionally provided between the metal electrode 11 and the light-emitting layer 12 of FIG. 1A. Light emission and electron/hole transporting functions are separated to establish a more effective carrier-blocking construction. As a result, the element can emit light efficiently. For example, an oxadiazole derivative or Alq, Bphen, or BCP shown below can be used for the electron-transporting layer 16.

Figure 1C:
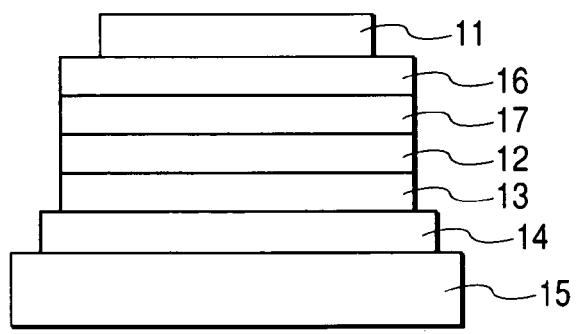

In addition, as shown in FIG. 1C, the exciton diffusion preventive layer 17 can be provided such that an exciton to be generated in the light-emitting layer 12 is trapped in the light-emitting layer 12 to perform efficient light emission.

Figure 1D:
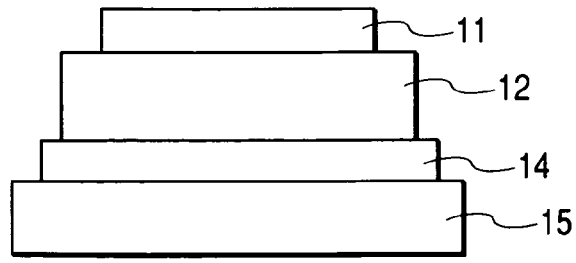

In addition, as shown in FIG. 1D, the element can be constructed by using only one organic layer. The element, which is often used in the application of a high molecular weight substance, can be used in vacuum evaporation of a low molecular weight substance.

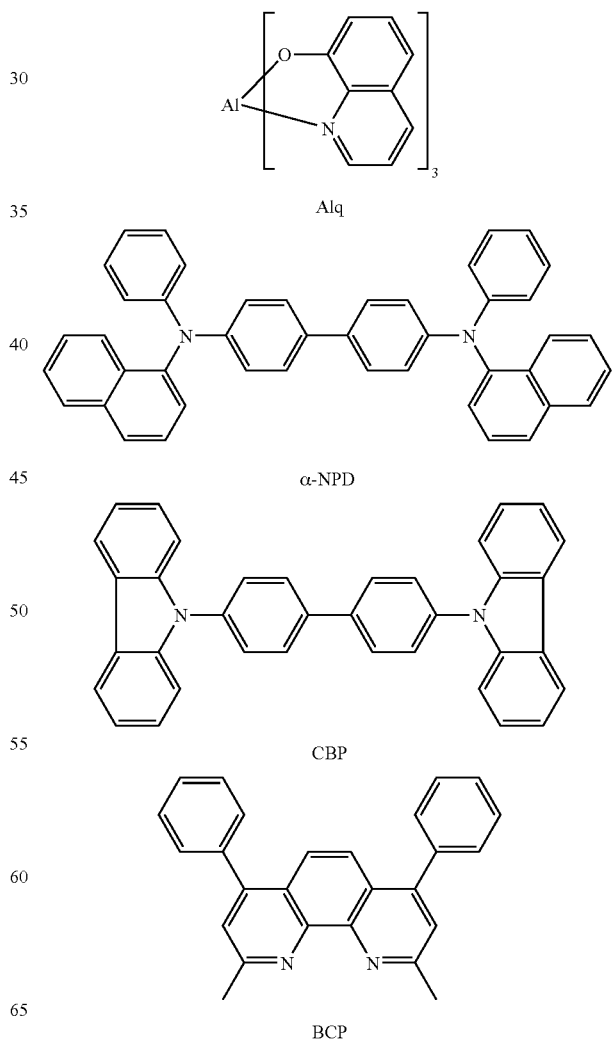

-continued

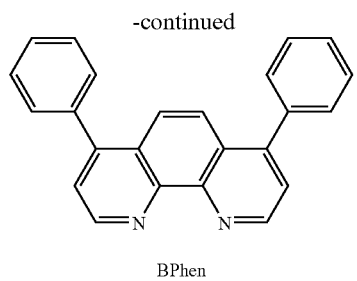

BPhen

The high-efficiency light-emitting device of the present invention can be applied to products that require energy savings and high intensity. Possible application examples thereof include: light sources for display devices, lighting units, and printers; and backlights for liquid crystal display devices. Possible display devices include a high-visibility and light-weight flat panel display that can provide energy savings. In addition, with regard to a light source for a printer, the light-emitting device of the present invention can replace a laser light source of a laser beam printer which has been widely used at present. Elements that can be addressed independently are arranged on an array to carry out desired exposure on a photosensitive drum, thereby forming an image. The use of the element of the present invention can remarkably reduce a device volume. With regard to lighting units and backlights, an energy savings effect can be expected from the present invention.

EXAMPLES 1 TO 10

Figure 2:
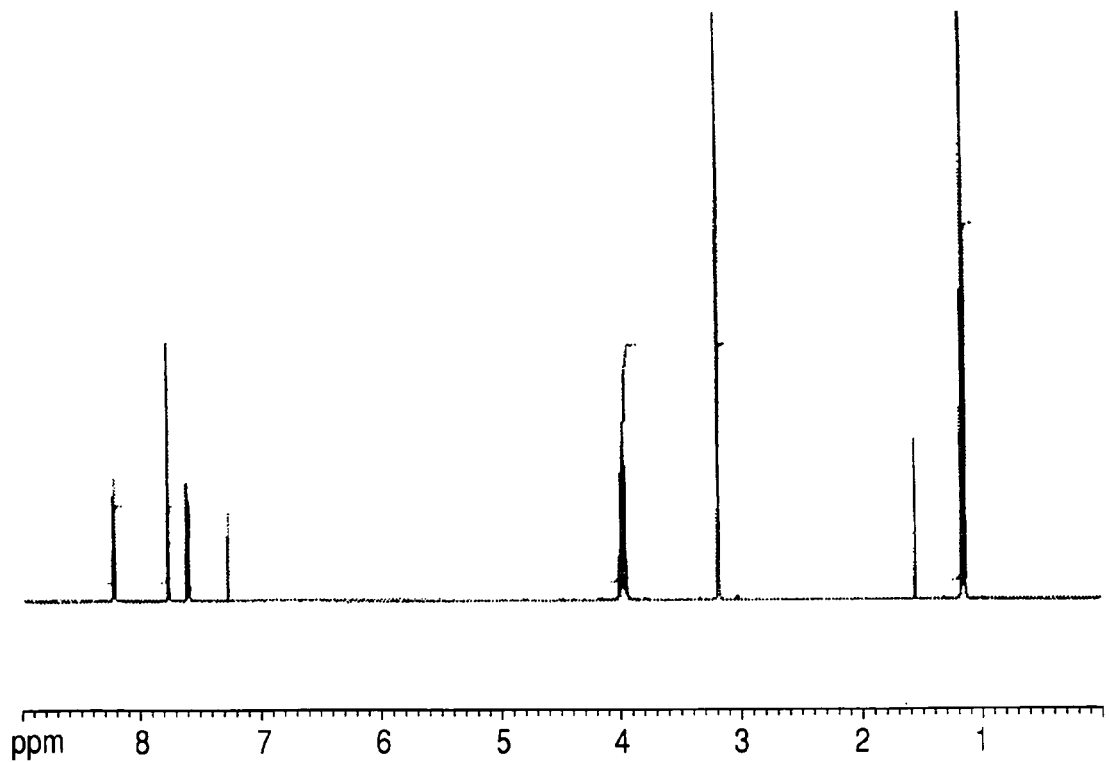
FIG. 2 is a ¹H-NMR chart of Exemplified Compound 326.
Figure 3:
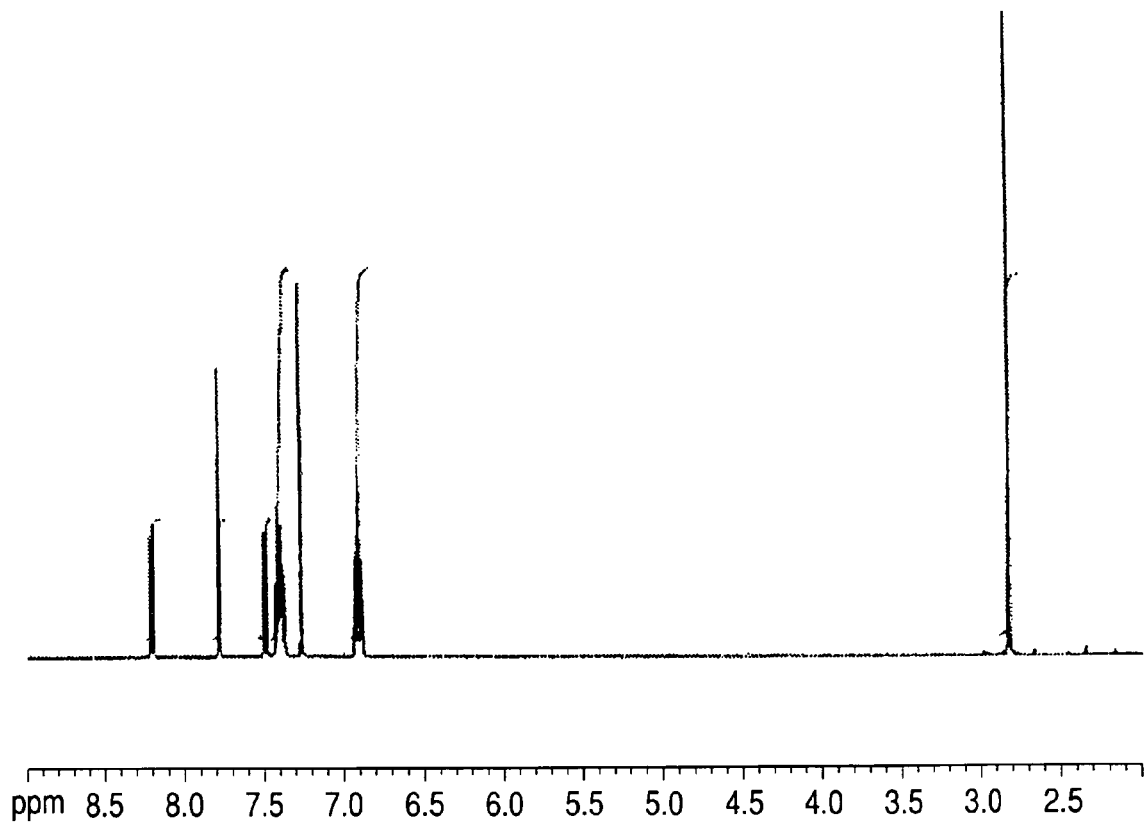
FIG. 3 is a ¹H-NMR chart of Exemplified Compound 335.

Compounds listed in Table 10 were synthesized according to the formula (A). Their structures were identified through $^1$H-NMR (Bruker DPX-400 NMR) and elemental analysis (Vario EL CHNOS). FIGS. 2 and 3 show $^1$H-NMR charts of Exemplified Compounds 326 and 335, respectively. Elemental analyses of the compounds agreed well with the calculated values for their weight ratios of elements C, H, and N.

In addition, their light-emitting properties by photoexcitation were measured. Table 10 shows the results. Their emission spectra were measured by using an F4500 (manufactured by Hitachi Instruments Service Co., Ltd., having an excitation wavelength in the range of 380 to 450 nm). The measurement was performed while all the compounds were in powder states. Their luminescent colors ranged from yellowish orange to red.

TABLE 10

| Example | Exemplified Compound No. | Light emission spectrum peak λmax (nm) |
| --- | --- | --- |
| 1 | 101 | 593 |
| 2 | 102 | 610 |
| 3 | 138 | 608 |
| 4 | 251 | 592 |
| 5 | 274 | 605 |
| 6 | 326 | 601 |
| 7 | 332 | 620 |
| 8 | 335 | 578 |
| 9 | 363 | 600 |
| 10 | 368 | 592 |

Figure 4:
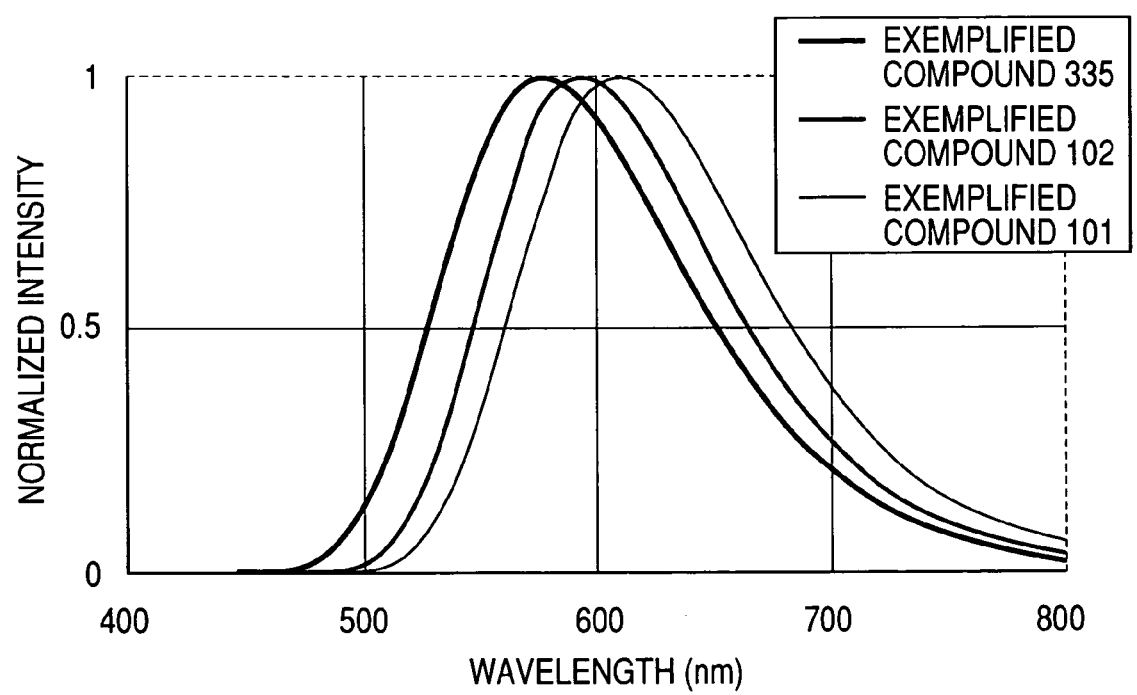
FIG. 4 shows emission spectra of Exemplified Compounds 101, 102, and 335.

Strong light emission was obtained in each compound in a solid state. FIG. 4 shows the emission spectra of Exemplified Compounds 101, 102, and 335.

EXAMPLES 11 AND 12

In each example, an organic EL element was prepared by using Exemplified Compound 101 synthesized in Example 1 or Exemplified Compound 102 synthesized in Example 2 as a light-emitting material.

The element construction employed was one having only one organic layer as shown in FIG. 1D. ITO of 100 nm in thickness (corresponding to the transparent electrode 14) was patterned on a glass substrate (corresponding to the transparent substrate 15) to have an electrode area of 3 mm$^2$.

An organic layer of 120 nm in thickness (corresponding to the light-emitting layer 12) was formed on the ITO substrate by spin-coating a solution containing the following compounds under a nitrogen atmosphere at 2,000 rpm for 20 seconds.

| | |
| --- | --- |
| Chlorobenzene: | 10 g |
| Polyvinyl carbazole (having an average molecular weight of 9,600): | 100 mg |
| Exemplified Compound 101 or 102: | 3.0 mg |

After the film formation, the substrate was loaded into a vacuum evaporation chamber to form a cathode having the following construction (corresponding to the metal electrode 11).

A metal electrode layer 1 (15 nm): AlLi alloy (containing 1.8 wt % of Li)

A metal electrode layer 2 (100 nm): Al

Element properties were evaluated by applying a DC voltage to each element with the metal electrode 11 as a negative electrode and the transparent electrode 14 as a positive electrode.

The volt-ampere characteristics of the elements exhibited good rectifying properties. The emission spectra of the elements were measured by using a spectrum measuring instrument SR1 manufactured by Topcon Corporation. Their emission spectra were longer than those obtained in Examples 1 and 2 by about 10 nm. The luminous efficiency of each of the elements upon application of a voltage of 14 V was calculated to be 0.3 lm/W and 0.5 lm/W. The elements provided stable light emission even when they were made to emit light upon conduction for 50 hours.

EXAMPLES 13 AND 14

In each example, a single bit organic EL element shown in FIG. 1B having three organic layers consisting of the hole-transporting layer 13, the light-emitting layer 12, and the electron-transporting layer 16 was prepared by using Exemplified Compound 101 synthesized in Example 1 or Exemplified Compound 251 synthesized in Example 4. Then, the element properties were measured.

A no alkali glass substrate was used as the transparent electrode 15. Then, indium tin oxide (ITO) of 100 nm in thickness was formed as the transparent electrode 14 on the transparent substrate 15 according to a sputtering method, and was patterned into an electrode of 2 mm in diameter.

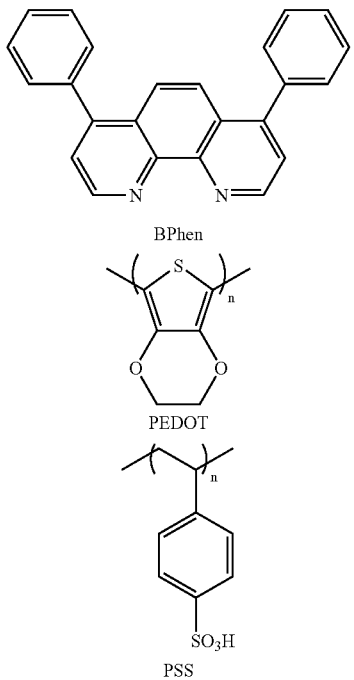

BPhen

PEDOT

PSS

A high molecular weight film solution containing PEDOT and PSS represented by the above structural formulae was spin-coated on the transparent electrode 14 to form the hole-transporting layer 13 of 30 nm in thickness. A 1.0% chloroform solution of each of Exemplified Compounds 101 and 251 was spin-coated twice on the hole-transporting layer 13 and dried in an oven at 60° C. for 60 minutes to obtain the light-emitting layer 12 of 70 nm in thickness. The light-emitting layer 12 was formed only of a copper coordination compound. Furthermore, a compound represented by Bphen above was subjected to resistance heating evaporation at a degree of vacuum of $10^{-4}$ Pa to obtain an organic layer of 40 nm in thickness as the electron-transporting layer 16.

Potassium fluoride (KF) was arranged with a thickness of 5 nm on the electron-transporting layer 16 to serve as an under coating layer of the metal electrode 11. Furthermore, an aluminum (Al) film of 100 nm in thickness was evaporated as the metal electrode 11 to form a cathode layer, thereby preparing an organic EL element.

The properties of the organic EL elements were measured as follows. The volt-ampere characteristics of the elements were measured by using a micro-ammeter 4140B manufactured by Hewlett-Packard and the light-emitting intensity of each element was measured by using a BM7 manufactured by Topcon Corporation. Each element of the examples exhibited good rectifying property.

The present EL elements were observed to emit light upon application of a voltage of 15 V. Their light emission wavelength peaks were at 595 nm and 597 nm. Light emission wavelengths nearly the same as those of Examples 1 and 4 were observed. The luminous efficiency at this time was 0.8 lm/W. In other words, stable light emission was obtained.

EXAMPLE 15

An organic EL element was prepared in the same manner as in each of Examples 13 and 14 except that organic layers were formed according to a vacuum evaporation method. It should be noted that α-NPD shown as 61 to 67 was used as a material for the hole-transporting layer 13, Exemplified Compound 326 synthesized in Example 6 was used for the light-emitting layer 12, and Bphen used in each of Examples 13 and 14 was used for the electron-transporting layer 16. Each layer had a thickness of 40 nm.

Electrical optical properties of the element were measured in the same manner as in each of Examples 13 and 14. The light emission wavelength peak of the element was at 610 nm upon application of a voltage of 10 V. A light emission wavelength nearly the same as that of Example 6 was observed. The luminous efficiency at this time was 0.6 lm/W. In other words, stable light emission was obtained.

As described above by way of the embodiment and examples, the light-emitting material of the present invention provides high luminous efficiency and high stability, and is available at a low cost. Therefore, the light-emitting material of the present invention is useful for a light-emitting material for an organic EL element.

What is claimed is:

1. A light-emitting device comprising a light-emitting layer containing a light-emitting material between a pair of electrodes, said light-emitting material comprising a metal coordination compound having a partial structure represented by a following general formula (1):

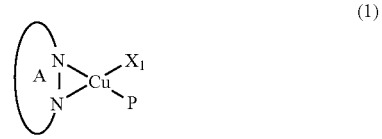

(wherein:
Cu represents a copper ion;
a ligand A is represented by a following structural formula:

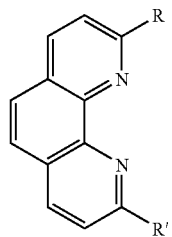

(wherein: R and R' each represent one of a straight-chain, branched, or cyclic alkyl group and an aromatic cyclic group that may have a substituent, and R and R' may be identical to or different from each other; a $CH_2$ group in the alkyl group may be substituted by one of —O— and —NH—; an H atom may be substituted by one of an aromatic cyclic group and a halogen atom; and one of R and R' may be a hydrogen atom);
an atom P that coordinates with Cu is a phosphorus atom of a phosphine compound represented by $PR_1R_2R_3$ ($R_1$, $R_2$, and $R_3$ in $PR_1R_2R_3$ each represent one of a straight-chain, branched, or cyclic alkyl group and an aromatic cyclic group that may have a substituent, and $R_1$, $R_2$, and $R_3$ may be identical to or different from one another, a $CH_2$ group in the alkyl group may be substituted by one of —O— and —NH—, a H atom may be substituted by one of an aromatic cyclic group and a halogen atom;

an atom of $X_1$ that coordinates with Cu is selected from the group consisting of a halogen atom, an oxygen atom, a sulfur atom, and a nitrogen atom; and one of $R_1$, $R_2$, and $R_3$ in $PR_1R_2R_3$ may contain $X_1$ to form a bidentate ligand).

2. The light-emitting device according to claim 1, wherein the metal coordination compound comprises an electrically neutralized nonionic compound.

3. The light-emitting device according to claim 1, wherein $X_1$ comprises −1 valent monodentate ligand and the atom of $X_1$ that coordinates with Cu is selected from the group consisting of a halogen atom, a nitrogen atom in an aromatic cyclic group that may have a substituent, an oxygen atom in —OR, and a sulfur atom in —SR (R in one of —OR and —SR is one of a straight-chain, branched, or cyclic alkyl group and an aromatic cyclic group that may have a substituent, a $CH_2$ group in the alkyl group may be substituted by one of —O— and —NH—, a H atom may be substituted by one of an aromatic cyclic group and a halogen atom).

4. The light-emitting device according to claim 1, wherein the copper ion comprises a +1 valent ion.

5. The light-emitting device according to claim 1, wherein the light-emitting material is present only in the light-emitting layer.

* * * * *

UNITED STATES PATENT AND TRADEMARK OFFICE
CERTIFICATE OF CORRECTION

| | |
|---|---|
| PATENT NO. | : 7,279,233 B2 |
| APPLICATION NO. | : 10/886570 |
| DATED | : October 9, 2007 |
| INVENTOR(S) | : Akira Tsuboyama et al. |

It is certified that error appears in the above-identified patent and that said Letters Patent is hereby corrected as shown below:

COLUMN 31

Line 16, "–1 valent" should read --a –1 valent--.

Signed and Sealed this

Seventeenth Day of June, 2008

JON W. DUDAS
*Director of the United States Patent and Trademark Office*